(12) United States Patent
Kurosaki et al.

(10) Patent No.: US 11,426,564 B2
(45) Date of Patent: Aug. 30, 2022

(54) METHOD AND APPARATUS FOR FORMING DRUG COATING LAYER

(71) Applicant: TERUMO KABUSHIKI KAISHA, Tokyo (JP)

(72) Inventors: Yasuo Kurosaki, Kanagawa (JP); Hiroshi Goto, Kanagawa (JP); Yuno Kitagawa, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 143 days.

(21) Appl. No.: 16/802,687

(22) Filed: Feb. 27, 2020

(65) Prior Publication Data

US 2020/0197674 A1    Jun. 25, 2020

Related U.S. Application Data

(63) Continuation of application No. PCT/JP2018/035041, filed on Sep. 21, 2018.

(30) Foreign Application Priority Data

Sep. 21, 2017  (JP) .............................. JP2017-181788

(51) Int. Cl.
*A61M 25/10* (2013.01)
*A61L 29/08* (2006.01)
*A61L 29/16* (2006.01)

(52) U.S. Cl.
CPC ......... *A61M 25/1029* (2013.01); *A61L 29/08* (2013.01); *A61L 29/16* (2013.01);
(Continued)

(58) Field of Classification Search
CPC ......... A61L 20/08; A61L 29/08; B29C 53/08; A61M 25/1029
See application file for complete search history.

(56) References Cited

U.S. PATENT DOCUMENTS 6,988,881 B2 *  1/2006 Motsenbocker .. A61M 25/1002
                                                                29/237
7,264,458 B2    9/2007 Holman et al.
(Continued)

FOREIGN PATENT DOCUMENTS

CN          1655833 A     8/2005
CN        101589971 A    12/2009
(Continued)

OTHER PUBLICATIONS

Kirsh, Balloon catheters: What are some key design considerations?, 2016, Medical Design and Outsourcing, pp. 1-9 (Year: 2016).*

(Continued)

*Primary Examiner* — Dah-Wei D. Yuan
*Assistant Examiner* — Andrew J Bowman
(74) *Attorney, Agent, or Firm* — Buchanan Ingersoll & Rooney PC

(57) ABSTRACT

A method and apparatus are disclosed for forming a drug coating layer capable of preventing breakage of elongated drug crystals on a surface of a balloon and maintaining the drug crystals in an appropriate shape in order to act on a living body. The method includes supplying a coating solution which contains the water-insoluble drug, a water-soluble additive, an organic solvent, and water to the surface of the balloon and evaporating the organic solvent and the water to form an additive layer containing the water-soluble additive and a protruding crystal having a tip end protruding from the additive layer, cutting a surplus portion protruding from the additive layer of the protruding crystal from a part surrounded by the additive layer and forming the part surrounded by the additive layer as the elongated body, and removing the cut-out surplus portion from the drug coating layer.

17 Claims, 8 Drawing Sheets

(52) U.S. Cl.
CPC ... *A61L 2300/204* (2013.01); *A61L 2300/216* (2013.01); *A61L 2300/416* (2013.01); *A61L 2420/02* (2013.01); *A61M 2025/105* (2013.01); *A61M 2025/1031* (2013.01); *A61M 2207/10* (2013.01)

(56) References Cited

U.S. PATENT DOCUMENTS

| | | |
|---|---|---|
| 2002/0123505 A1 | 9/2002 | Mollison et al. |
| 2008/0118544 A1 | 5/2008 | Wang |
| 2011/0008405 A1 | 1/2011 | Birdsall et al. |
| 2011/0015664 A1 | 1/2011 | Kangas et al. |
| 2013/0095226 A1 | 4/2013 | Shinoda et al. |
| 2013/0197436 A1 | 8/2013 | Wang |
| 2013/0337147 A1 | 12/2013 | Chappa et al. |
| 2014/0004253 A1 | 1/2014 | Ruane |
| 2014/0271775 A1 | 9/2014 | Cleek et al. |
| 2014/0358122 A1 * | 12/2014 | Yamashita ............ A61M 25/10 604/509 |
| 2015/0057746 A1 | 2/2015 | Yamashita et al. |
| 2015/0182732 A1 | 7/2015 | Zeng et al. |
| 2016/0058915 A1 | 3/2016 | D'Onofrio et al. |
| 2017/0014601 A1 | 1/2017 | Kurosaki et al. |

FOREIGN PATENT DOCUMENTS

| | | |
|---|---|---|
| CN | 101610798 A | 12/2009 |
| CN | 102596277 A | 7/2012 |
| CN | 102811749 A | 12/2012 |
| CN | 103611212 A | 3/2014 |
| CN | 204582174 U | 8/2015 |
| EP | 1 251 899 B1 | 4/2012 |
| JP | 2014131748 A | 7/2014 |
| JP | 2015521530 A | 7/2015 |
| JP | 2016513543 A | 5/2016 |
| JP | 6272849 B2 | 1/2018 |
| WO | 2013146376 A1 | 10/2013 |
| WO | 2015151877 A1 | 10/2015 |

OTHER PUBLICATIONS

An English Translation of the International Search Report (Form PCT/ISA/210) and the Written Opinion of the International Searching Authority (Form PCT/ISA/237) dated Dec. 11, 2018, by the Japanese Patent Office in corresponding International Application No. PCT/JP2018/035041. (7 pages).

The extended European Search Report dated Jun. 25, 2020, by the European Patent Office in corresponding European Patent Application No. 18859371.9-1109. (7 Pages).

International Search Report (PCT/ISA/210) dated Dec. 11, 2018, by the Japan Patent Office as the International Searching Authority for International Application No. PCT/JP2018/035041.

Written Opinion (PCT/ISA/237) dated Dec. 11, 2018, by the Japan Patent Office as the International Searching Authority for International Application No. PCT/JP2018/035041.

Office Action (First Office Action) dated Jul. 1, 2021, by the State Intellectual Property Office of People's Republic of China in corresponding Chinese Patent Application No. 201880052039.4 and an English Translation of the Office Action. (13 pages).

* cited by examiner

METHOD AND APPARATUS FOR FORMING DRUG COATING LAYER

CROSS-REFERENCES TO RELATED APPLICATIONS

This application is a continuation of International Application No. PCT/JP2018/035041 filed on Sep. 21, 2018, which claims priority to Japanese Application No. 2017-181788 filed on Sep. 21, 2017, the entire content of both of which is incorporated herein by reference.

FIELD OF THE DISCLOSURE

The present disclosure generally relates to a method and apparatus for forming a drug coating layer provided on a surface of a balloon.

BACKGROUND DISCUSSION

In recent years, a balloon catheter has been used in order to improve lesion areas (stenosed sites) generated in a body lumen. Generally, the balloon catheter includes an elongated shaft portion and a balloon capable of inflating in a radial direction and provided on a distal side of the shaft portion. After the balloon in a deflated state reaches a target area in a body via a small body lumen, the balloon is inflated and the lesion area is thus widened.

However, when the lesion area is forcibly widened, excessive proliferation of smooth muscle cells may occur to induce new stenosis (restenosis) in the lesion area. For this reason, recently, a drug eluting balloon (DEB) in which a surface of the balloon is coated with a drug for preventing stenosis has been used. The drug elution balloon can instantaneously release the drug coated on the surface of the balloon by being inflated to the lesion area, thereby preventing restenosis.

In recent years, it has been becoming apparent that a morphological form of the drug coated on the surface of the balloon affects a releasing property of the drug from the balloon surface or tissue transferability in the lesion area. For example, U.S. Patent Application Publication No. 2014/0271775 discloses a balloon catheter in which drug crystals with an elongated shape are formed on the surface of the balloon.

An example of a balloon catheter in which an adhesive layer, a first layer containing a treatment agent and an additive, and a second layer containing an additive are provided on a surface of a balloon is disclosed in Japanese Patent Application Publication No. 2014-131748.

The elongated crystals formed on the surface of the balloon may be broken due to their relatively long and thin shape. For example, since a force is applied to the surface of the balloon when the balloon is folded, the elongated crystals are likely to be broken. When the crystals are broken, the broken crystals are fallen off from the balloon at the time of transporting the balloon in a blood vessel, resulting in an undesirable effect on a living body.

SUMMARY

In accordance with an aspect, a method and apparatus are disclosed for forming a drug coating layer capable of preventing breakage of elongated drug crystals on a surface of a balloon and maintaining the drug crystals in an appropriate shape in order to act on the living body.

In accordance with another aspect, a method for forming a drug coating layer in which a plurality of elongated bodies which are crystals of a water-insoluble drug and each have a long axis are formed on a surface of a balloon, and the method includes supplying a coating solution which contains the water-insoluble drug, a water-soluble additive, an organic solvent, and water to the surface of the balloon and evaporating the organic solvent and the water to form an additive layer containing the water-soluble additive and a protruding crystal which is an elongated drug crystal having a tip end protruding from the additive layer, cutting out a surplus portion protruding from the additive layer of the protruding crystal from a part surrounded by the additive layer and forming the part surrounded by the additive layer as the elongated body, and removing the cut-out surplus portion from the drug coating layer.

In accordance with a further aspect, an apparatus is disclosed for forming a drug coating layer in which a plurality of elongated bodies which are water-insoluble drug crystals and each have a long axis is formed on a surface of a balloon, and the apparatus includes a rotating mechanism section applying a rotational force to the balloon, a coating solution supply section applying a coating solution which contains a water-insoluble drug, a water-soluble additive, an organic solvent, and water to an outer surface of the rotating balloon, a pressing section pressing the surface of the balloon and cutting out a part of the drug crystal formed on the surface of the balloon, and a gas supply section removing the cut-out drug crystal by blowing gas to the surface of the balloon.

In the method for forming a drug coating layer as described above, since the surplus portion protruding from the additive layer of the drug crystal is removed, the elongated body which is surrounded by the additive layer and a drug crystal can be obtained, which is not easily broken. Therefore, the breakage of the elongated body on the surface of the balloon can be prevented and the elongated body in an appropriated shape can be maintained in order to act on the living body.

The additive layer may contain a water-soluble low molecular weight compound. Thus, the additive layer can be rapidly dissolved in the blood vessel, and thus does not interfere with the transferability in blood vessel of the elongated body which is a drug.

In the removing of the surplus portion, the surplus portion may be removed from the drug coating layer by blowing gas to the surface of the balloon. Thus, the surplus portion separated from the elongated body can be prevented from being affected to the living body by entering the living body without remaining the surplus portion on the balloon.

In the removing of the surplus portion, the surplus portion may be removed from the drug coating layer by applying vibration to the surface of the balloon. Thus, the surplus portion separated from the elongated body can be prevented from being affected to the living body by entering the living body without remaining the surplus portion on the balloon.

The removing the surplus portion can include forming a pleat portion protruding outward in the radial direction of the balloon after the protruding crystal is formed, and folding the pleat portion along a circumferential direction of the balloon. In at least one of the forming the pleat portion and the folding the pleat portion, a force may be applied to the surplus portion protruding from the additive layer of the protruding crystal, and the surplus portion may thus be cut out from the elongated body. Thus, in the process of folding the balloon, the surplus portion of the drug crystal can be rather effectively removed.

The water-insoluble drug may contain at least one water-insoluble drug selected from the group consisting of rapamycin, paclitaxel, docetaxel, and everolimus. Thus, it is possible to properly prevent restenosis of the stenosed site in the blood vessel due to the elongated body which is a drug crystal.

In the apparatus for forming a drug coating layer as described above, a part of the drug crystal formed on the surface of the balloon can be cut out by the pressing section, and thus a part of the cut-out drug crystal can be removed by the gas supply section. Therefore, the drug crystal separated from the elongated body can be prevented from being affected to the living body by entering the living body without remaining the drug crystal on the balloon.

The forming apparatus may further include a vibrating section configured to vibrate the balloon. Thus, a part of the cut-out drug crystals can be removed due to the vibration. Therefore, the drug crystal separated from the elongated body can be prevented from being affected to the living body by entering the living body without remaining the drug crystal on the balloon.

In accordance with another aspect, a method for forming a drug coating layer on a balloon of a balloon catheter, the method comprising: supplying a coating solution which contains a water-insoluble drug, a water-soluble additive, an organic solvent, and water to a surface of the balloon; evaporating the organic solvent and the water from the coating solution to form an additive layer containing the water-soluble additive and protruding elongated drugs crystals having a tip end protruding from the additive layer; and cutting a surplus portion protruding from the additive layer of the protruding crystal from a part surrounded by the additive layer and forming the part surrounded by the additive layer as the elongated body.

BRIEF DESCRIPTION OF THE DRAWINGS

FIGS. 13A-13C are cross-sectional views illustrating the balloon folded by a balloon folding apparatus, wherein FIG. 13A illustrates a state before the balloon is folded, FIG. 13B illustrates a state in which the pleat portions are formed by the pleating section, and FIG. 13C illustrates a state in which the pleat portions are folded by the folding section.

DETAILED DESCRIPTION

Set forth below with reference to the accompanying drawings is a detailed description of embodiments of a method and apparatus for forming a drug coating layer provided on a surface of a balloon representing examples of the inventive a method and apparatus for forming a drug coating layer provided on a surface of a balloon. The dimensions of the drawings may be exaggerated or different from the actual ratios for convenience of description and illustration.

Figure 1:
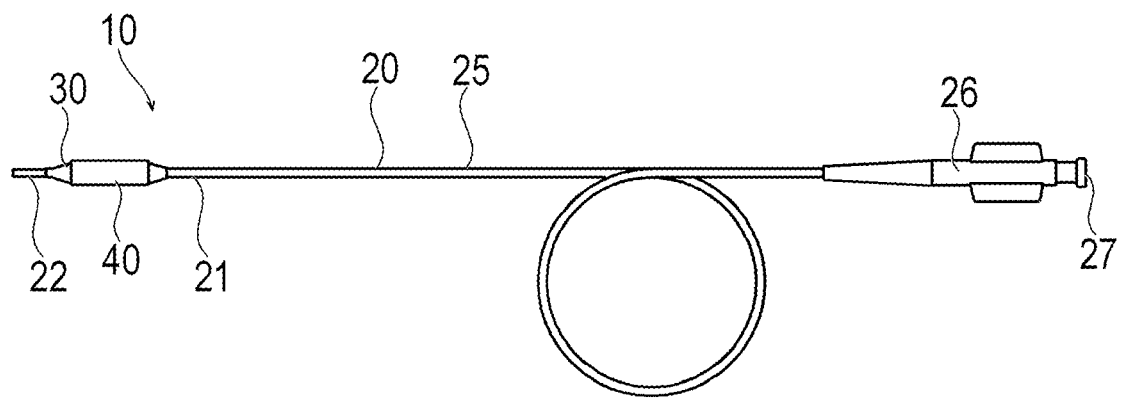
FIG. 1 is a front view illustrating a balloon catheter having a drug coating layer according to a first embodiment.
Figure 2:
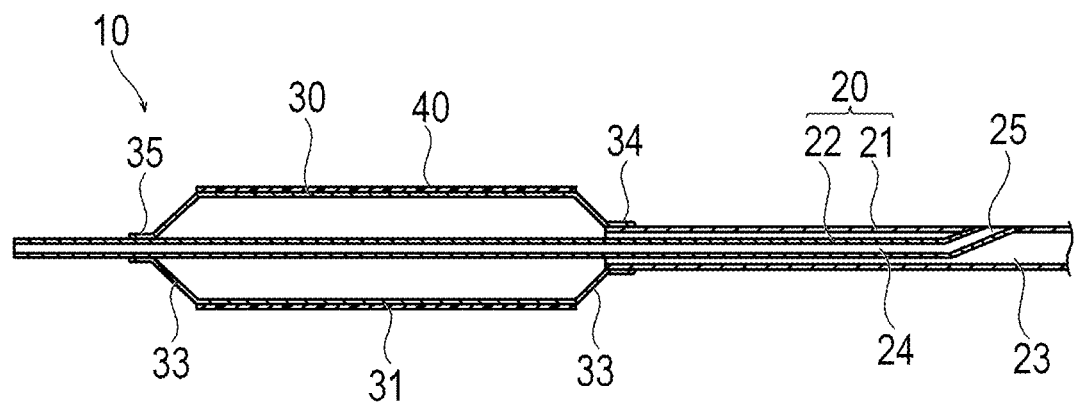
FIG. 2 is a cross-sectional view of a distal portion of the balloon catheter.
Figure 3:
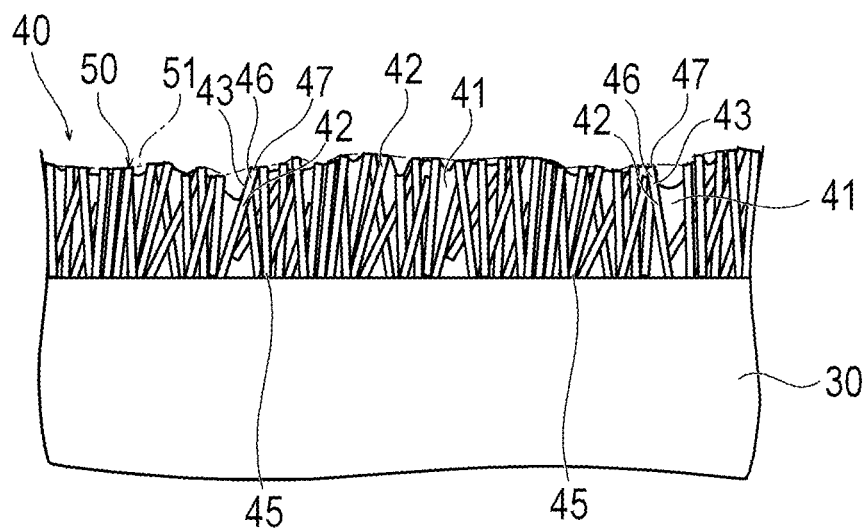
FIG. 3 is a cross-sectional view illustrating the drug coating layer on a surface of the balloon.

According to a method for forming a drug coating layer according to a first embodiment of the present disclosure, a drug coating layer 40 is formed on a surface of a balloon 30 of a drug eluting type balloon catheter 10 as illustrated in FIGS. 1 to 3. In the present specification, a side of the balloon catheter 10 to be inserted into a body lumen refers to a "distal side" and an operating hand-side refers to a "proximal side".

A configuration of the balloon catheter 10 is described herein. The balloon catheter 10 includes an elongated catheter main body 20, the balloon 30 provided on a distal portion of the catheter main body 20, the drug coating layer 40 provided on the surface of the balloon 30, and a hub 26 fixed to a proximal end of the catheter main body 20.

The catheter main body 20 includes an outer tube 21 which is a tube body in which the distal end and the proximal end are open and an inner tube 22 which is a tube body disposed or positioned inside or inserted into the outer tube 21. The inner tube 22 is housed inside a hollow of the outer tube 21, and a distal portion of the catheter main body 20 has a double tube structure. In the hollow of the inner tube 22, a guide wire lumen 24 for inserting guide wire is provided. In addition, an inflation lumen 23 for circulating inflation fluid in the balloon 30 is formed inside the hollow of the outer tube 21, that is, outside the inner tube 22. The inner tube 22 is opened to the outside of an opening portion 25. The inner tube 22 protrudes further toward a distal side than the distal end of the outer tube 21. A distal tip as a separate member may be provided at the distal portion of the inner tube 22.

In the balloon 30, a balloon fusing section (balloon fixing section) 34 at a proximal end portion is fused (fixed) at the distal portion of the outer tube 21 and a balloon fusing section (balloon fixing section) 35 at a distal end portion is fused (fixed) at the distal portion of the inner tube 22. A method for fixing the balloon 30 to the outer tube 21 and the inner tube 22 is not limited to the fusing, and for example, may be adhered. Thus, the inside of the balloon 30 communicates with the inflation lumen 23. The inflation fluid is injected to the balloon 30 through the inflation lumen 23, such that the balloon 30 can be inflated. In accordance with an exemplary embodiment, the inflation fluid may be gas or liquid, and for example, gases such as helium gas, $CO_2$ gas, $O_2$ gas, $N_2$ gas, Ar gas, air, and mixed gases, or liquids such as a saline solution and a contrast agent can be used as the inflation fluid.

At a central portion of the balloon 30 in an axial direction, a cylindrical straight section 31 (inflatable portion) having an outer diameter equal to an outer diameter of the balloon is formed at the time of inflating the balloon and a tapered portion 33 having an outer diameter being gradually changed is formed at both sides of the straight section 31 in the axial direction. The drug coating layer 40 containing a drug is then formed on the entire surface of the straight section 31. In the balloon 30, a range in which the drug coating layer 40 is formed is not limited only to the straight section 31, and may include at least a part of the tapered portion 33 in addition to the straight section 31 or only a part of the straight section 31.

A proximal opening portion 27, which serves as a port communicating with the inflation lumen 23 of the outer tube 21 and to allow the inflation fluid to flow in and out, is formed at the hub 26.

A length of the balloon 30 in the axial direction is not particularly limited, and may preferably, for example, be 5 mm to 500 mm, more preferably 10 mm to 300 mm, and still more preferably 20 mm to 200 mm. An outer diameter of the balloon 30 at the time of inflating is not particularly limited, and may preferably, for example, be 1 mm to 10 mm and more preferably 2 mm to 8 mm.

A surface of the balloon 30 before the drug coating layer 40 is formed or applied is smooth and nonporous. The surface of the balloon 30 before the drug coating layer 40 is formed may have recesses or blind holes which do not penetrate a film forming the balloon. In addition, the surface of the balloon 30 before the drug coating layer 40 is formed or applied may be both a smooth, nonporous surface and a surface having blind holes or recesses which do not penetrate the film. That is, some parts of the surface of the balloon 30 before the drug coating layer 40 is applied may be a smooth, nonporous surface and other parts of the surface of the balloon 30 before the drug coating layer 40 is applied may have blind holes or recesses. The blind holes (recesses) may have, for example, a diameter of from 0.1 µm to 5 µm and a depth of from 0.1 µm to 10 µm. As described in more detail below, the drug coating layer preferably includes upstanding elongated crystals of a water-insoluble drug. The diameter and depth of the blind holes noted above are selected so that the blind holes individually receive one of the elongated crystals (e.g., the proximal end of one elongated crystal is positioned in one blind hole, the proximal end of another elongated crystal is received in a different blind hole, etc.) or so that each of a plurality of the blind holes receives a portion of one of the elongated crystals (e.g., one portion of the proximal end of an elongated crystal is received in one blind hole, another portion of the proximal end of the same elongated crystal is positioned in a different blind hole, etc.). In addition, the one or more blind holes may have, for example, a diameter of from 5 µm to 500 µm and a depth of from 0.1 µm to 50 µm. These size ranges for the diameter and depth may apply for blind holes that receive one elongated crystal (i.e., the proximal end of one elongated crystal is positioned in each blind hole or the proximal ends of more than one elongated crystal is positioned in each blind hole). Each of the blind holes that contains an elongated crystal, part of an elongated crystal or plural elongated crystals are configured so that the elongated crystals project out from the blind hole.

In accordance with an exemplary embodiment, it is preferable that the balloon 30 has both some flexibility, and simultaneously, some rigidity, so as to be inflated when the balloon 30 reaches the blood vessel, a tissue, or the like and release the drug contained in the surface of the balloon from the drug coating layer 40. Specifically, the balloon 30 can be made or formed of a metal or a resin, but at least the surface of the balloon 30 on which the drug coating layer 40 is provided is preferably formed of a resin. Examples of constituent materials of at least the surface of the balloon 30 include polyolefins such as polyethylene, polypropylene, polybutene, an ethylene-propylene copolymer, an ethylene-vinyl acetate copolymer, ionomer, or a mixture of two or more kinds of polyolefins, an ethylene-propylene copolymer, an ethylene-vinyl acetate copolymer, and a ionomer, and thermoplastic resins such as a soft polyvinyl chloride resin, polyamide, polyamide elastomer, nylon elastomer, polyester, polyester elastomer, polyurethane, and a fluororesin, silicone rubber, latex rubber, and the like. Among these, polyamides are preferable. That is, at least a part of the surface of the balloon 30 coated with the drug is made from polyamides. The polyamides are not particularly limited as long as it is a polymer having an amide bond and examples of the polymer having an amide bond can include aromatic polyamides, for example, homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), and polydodecanolactam (nylon 12), copolymers such as caprolactam/lauryllactam copolymer (nylon 6/12), caprolactam/aminoundecanoic acid copolymer (nylon 6/11), caprolactam/ω-aminononanoic acid copolymer (nylon 6/9), and caprolactam/hexamethylenediammonium adipate copolymer (nylon 6/66), copolymer of adipic acid with metaxylenediamine, and copolymers of hexamethylenediamine with m,p-phthalic acids, and the like. Furthermore, polyamide elastomers which are block copolymers having nylon 6, nylon 66, nylon 11, nylon 12, or the like as a hard segment and having a polyalkylene glycol, a polyether, an aliphatic polyester, or the like as a soft segment can also be used as a material for the balloon 30. The polyamides may be used alone or in combination of two or more kinds of polyamides. In certain embodiments, the balloon 30 has a smooth surface formed of polyamide.

The drug coating layer 40 is formed on the surface of the balloon 30 directly or through a pre-processing layer such as a primer layer by a method described below. As illustrated in FIG. 3, the drug coating layer 40 includes an additive layer 41 (diluting agent layer) containing a water-soluble low molecular weight compound and disposed on the surface of the balloon 30 in a form of layer, and a plurality of elongated bodies 42 which are crystals of the water-insoluble drug and each have an independent long axis (longitudinal axis or central axis). A proximal end 45 of the elongated body 42 directly comes into contact with the surface of the balloon 30. In addition, elongated bodies 42 in which the proximal end 45 does not come into contact with the surface of the balloon 30 may exist. The tip end 46 of the elongated body 42 may slightly protrude from the additive layer 41. Therefore, a length of a part of the elongated body 42 protruding from a surface of the additive layer 41 toward the outside can be shorter than a length of a part of the elongated body 42 being located in the additive layer 41. In accordance with an exemplary embodiment, the outer surface of the drug coating layer 40 does not have a constant height from the surface of the balloon 30 and can have an undulating shape to some extent. Therefore, the surface of the drug coating layer 40 can have an unevenness. The unevenness of the surface of the drug coating layer, for example, may be regular. The outer surface of the drug coating layer 40 is formed by the surface of the additive layer 41, a side surface 43 and a tip surface 47 of the elongated body 42 which are embedded in the additive layer 41 and located on a surface layer of the additive layer 41. That is, at least a portion of the side surface 43 and the tip surface 47 of at least some of the elongated bodies 42 may be exposed from the surface of the additive layer 41 (i.e., the tip surface of the elongated bodies may be exposed (i.e., not covered by the additive layer) and a part of the side surface of the elongated bodies may be exposed (i.e., not covered by the additive layer)).

In accordance with an exemplary embodiment, a plurality of elongated bodies 42 may be regularly arranged on the surface of the balloon 30. In other embodiments, the plurality of elongated bodies 42 may be irregularly arranged on the surface of the balloon 30.

An inclination angle of the long axis of the elongated body 42 to the surface of the balloon 30 is not particularly limited, and the inclination angle of the elongated body 42 to the surface of the balloon 30 can be, for example, 45 degrees to 135 degrees, preferably 60 degrees to 120 degrees, more preferably 75 degrees to 105 degrees, and still more preferably about 90 degrees.

An amount of drug contained in the drug coating layer 40 is not particularly limited, and the drug may be contained at a concentration, for example, of 0.1 µg/mm$^2$ to 10 µg/mm$^2$, preferably 0.5 µg/mm$^2$ to 5 µg/mm$^2$, more preferably 0.5 µg/mm$^2$ to 3.5 µg/mm$^2$, still more preferably 1.0 µg/mm$^2$ to 3 µg/mm$^2$. An amount of crystals of the drug coating layer 40 is not particularly limited, and preferably, for example, 5 crystals/10 µm$^2$ to 500,000 crystal/10 µm$^2$ (the number of crystals per 10 µm$^2$), more preferably 50 crystals/10 µm$^2$ to 50,000 crystals/10 µm$^2$, and still more preferably 500 crystals/10 µm$^2$ to 5,000 crystals/10 µm$^2$.

The plurality of the elongated bodies 42 each having an independent long axis may exist in a state in which the elongated bodies are combined. For example, the plurality of adjacent elongated bodies 42 may come into contact with each other in a state in which the adjacent elongated bodies have different angles from each other (i.e., in a state in which the elongated bodies are angled at different angles relative to a common orientation). The plurality of elongated bodies 42 may be positioned on the surface of the balloon such that adjacent elongated bodies 42 are spaced apart from one another so that a space exists between adjacent elongated bodies. In either case in which the plurality of elongated bodies 42 are in a combined state or wherein the plurality of elongated bodies 42 are spaced apart from each other, the elongated bodies 42 may exist on the surface of the balloon 30. The plurality of elongated bodies 42 may have different long axis directions and may be arranged in a circular shape as a brush shape. Each of the elongated bodies 42 exists independently, has a certain length, and one end (proximal end 45) of a part with the length is fixed to the additive layer 41 or the balloon 30. In certain embodiments, the elongated body 42 is not interlocked with the adjacent elongated body 42 without forming a complex structure. In an aspect, the long axis of the elongated body 42 may be substantially linear.

In accordance with an exemplary embodiment, it can be preferable that the elongated bodies 42 each stand-alone without being in contact with each other. The proximal end 45 of the elongated body 42 may be in contact with the other proximal end 45 on the balloon 30. In addition, the proximal end 45 of the elongated body 42 may stand alone without being in contact with the other proximal end 45 on the balloon 30.

The elongated bodies 42 may be hollow or solid. Hollow elongated bodies 42 and solid elongated bodies 42 may both exist on the surface of the balloon 30. In a case where the elongated body 42 is hollow, at least the tip end of the elongated body 42 is hollow. A cross section of the elongated body 42 in a plane at a right angle (perpendicular) to the long axis of the elongated body 42 has a hollow. The cross section of the elongated body 42 having the hollow in a plane at a right angle (perpendicular) to the long axis of the elongated body 42 is polygonal. The polygon can be, for example, a triangle, a tetragon, a pentagon, a hexagon, or the like. Therefore, the elongated body 42 has the tip end 46 (or the tip surface 47) and the proximal end 45 (or the proximal surface) and the side surface between the tip end 46 (or the tip surface 47) and the proximal end 45 (or the proximal surface) is formed as an elongated polyhedron constituted of a plurality of substantial planes. In addition, the elongated body 42 may have a needle shape. This crystal morphological form (crystal morphological form of a hollow elongated body) is constituted either entirely, or at least in part, of the plane on the surface in contact with the proximal end 45.

A length of the elongated bodies 42 having a long axis in the long axial direction may be, for example, preferably 5 µm to 20 µm, more preferably 9 µm to 11 µm, and still more preferably about 10 µm. A diameter of the elongated bodies 42 having a long axis may be, for example, preferably 0.01 µm to 5 µm, more preferably 0.05 µm to 4 µm, and still more preferably 0.1 µm to 3 µm.

In accordance with an exemplary embodiment, the elongated bodies 42 having the long axis described above has an amount equal to or more than 50% by volume and more preferably equal to or more than 70% by volume with respect to the total amount of drug crystals contained in the surface of the balloon 30.

In accordance with an exemplary embodiment, an aggregate (or cluster) 50 of the elongated bodies is formed of a plurality of the elongated bodies 42. The elongated bodies 42 in the aggregate (or cluster) 50 may include elongated bodies in contact with the balloon outer surface, elongated bodies spaced from the outer surface of the balloon 30 at different distances and elongated bodies oriented at different angles. The drug coating layer has an outer surface 51 located outside the aggregate 50 and connecting a plurality of tip ends 46 and side surfaces 43. The outer surface 51 of the drug coating layer has an unevenness. The additive layer 41 is provided in a space between the surface of the balloon 30 and the outer surface 51 of the drug coating layer. The tip ends 46 of the elongated bodies 42 may protrude slightly from the additive layer 41. The side surface 43 and/or tip surface 47 of the elongated bodies 42 located on the outer surface 51 can be exposed from the surface of the additive layer 41. The elongated body 42 which has no exposed portion embedded in the additive layer 41 can also exist. The additive layer 41 exists to be distributed into a space between the plurality of the elongated bodies 42 standing close together. The additive layer 41 may exist in a region where there are the elongated bodies 42 and may not exist in a region where there are no elongated bodies 42. In accordance with an exemplary embodiment, an additive constituting the additive layer 41 may not form a matrix. The additive constituting the additive layer 41 may form a matrix. The matrix is a layer in which relative polymer substances (polymers, or the like) are continuously constituted (i.e., formed), forms a mesh-shaped three-dimensional structure, and a relatively small space exists in the matrix. Therefore, the water-insoluble drug constituting crystals is not adhered to the matrix substances. The water-insoluble drug constituting crystals is not embedded in the matrix substances.

In accordance with an exemplary embodiment, the additive layer 41 is formed as a layer by coating the additive layer on the surface of the balloon 30 in a water-soluble state and then drying the additive layer 41. The additive layer 41 is an amorphous layer. The additive layer 41 may have crystal particles. In addition, the additive layer 41 may be formed as an independent layer that does not contain a water-insoluble drug. A thickness of the additive layer 41 is not particularly limited, and the thickness of the additive layer 41, for example, may be preferably 0.5 µm to 20 µm. A length of a part of the elongated body 42 protruding from the surface of the additive layer 41 toward the outside is not particularly limited, and the length of the part of the elongated body 42 protruding from the surface of the additive layer toward the outside, for example, may be 0 to 1 µm (i.e., slightly protruding).

At the time of delivering the drug to the body, the drug coating layer 40 including the elongated body 42 having the long axis exhibits relatively low toxicity and a high stenosis inhibiting effect. In a case where the elongated body 42 has a hollow crystal structure, since a unit of crystals becomes relatively small when the drug is transferred to a tissue, the elongated body has relatively good permeability to the tissue and relatively good solubility. Therefore, the drug is efficiently acted to help prevent stenosis. In addition, since the drug remaining in a tissue as a large mass is relatively small, the toxicity can be relatively low.

In addition, the drug coating layer 40 has the plurality of substantially uniform elongated bodies 42 each having a long axis and substantially uniform morphological forms standing on the surface being in contact with the proximal end 45 in parallel. Therefore, a size (a length in the long axis direction) of crystals transferred to the tissue can be as small as about 10 µm. Therefore, the drug can uniformly acted on a target lesion, such that the permeability in tissue is relatively high. Furthermore, since a dimension of crystals to be transferred is relatively small, an excessive amount of drug no longer remains in a target lesion in an excessive time. Therefore, it is considered that a relatively high stenosis inhibiting effect can be exhibited without exhibiting toxicity.

The drug coated on the surface of the balloon 30 may include an amorphous form. The crystals or amorphous forms may be arranged in the drug coating layer 40 so as to have regularity. In addition, the crystals or amorphous forms may be irregularly arranged.

Next, a balloon coating system for forming the above-described drug coating layer 40 on the balloon 30, will be described. This system includes a balloon coating apparatus 60 for forming the drug coating layer 40 on the balloon 30 (see FIG. 4) and a balloon folding apparatus for folding the balloon 30 on which the drug coating layer 40 is formed (see FIGS. 6 and 8).

Figure 4:
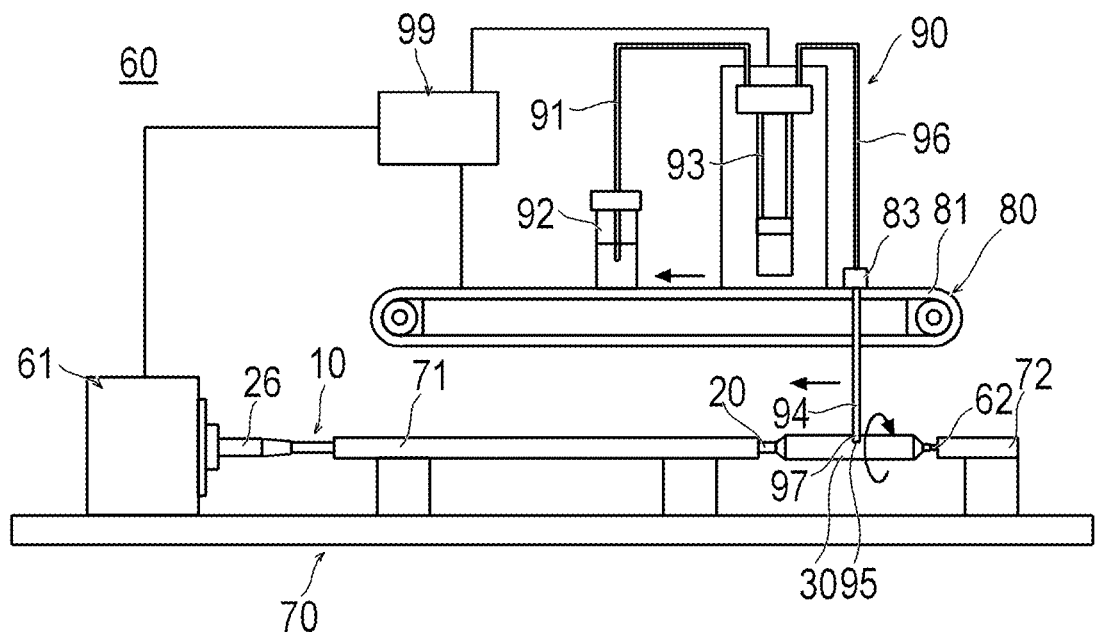
FIG. 4 is a front view illustrating a balloon coating apparatus.
Figure 5:
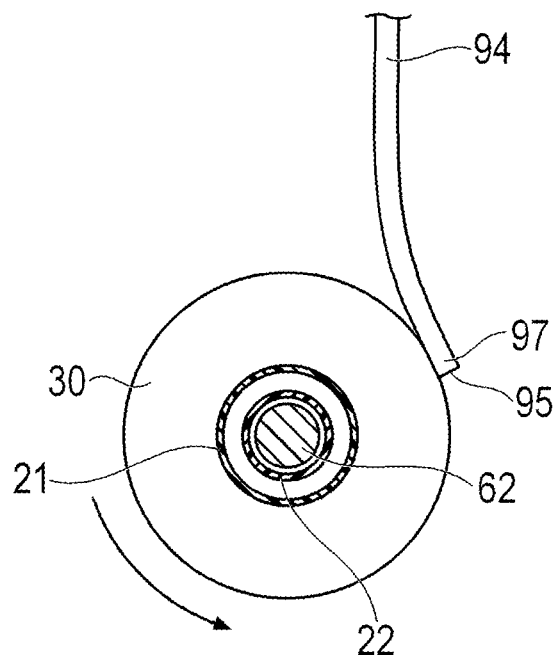
FIG. 5 is a cross-sectional view illustrating a dispensing tube in contact with the balloon.

First, the balloon coating apparatus 60 will be described. As illustrated in FIGS. 4 and 5, the balloon coating apparatus 60 includes a rotating mechanism section 61 rotating the balloon catheter 10 and a supporting table 70 for supporting the balloon catheter 10. The balloon coating apparatus 60 further includes an applying mechanism section 90 provided with a dispensing tube 94 that applies a coating solution to the surface of the balloon 30, a moving mechanism section 80 for moving the dispensing tube 94 to the balloon 30, and a control unit 99 controlling the balloon coating apparatus 60.

The rotating mechanism section 61 holds the hub 26 of the balloon catheter 10 and rotates the balloon catheter 10 around an axis of the balloon 30 by a driving source such as a motor built in the rotating mechanism section 61. A core 62 in the guide wire lumen 24 is inserted through the balloon catheter 10 and held, and the flow of the coating solution in the guide wire lumen 24 can be prevented by the core 62. In addition, since the balloon catheter 10 operates the circulation of the fluid to the inflation lumen 23, a three-way stopcock capable of controlling the opening and closing of a flow path is connected to the proximal opening portion 27 of the hub 26.

The supporting table 70 includes a pipe-shaped proximal support portion 71 accommodating the catheter main body 20 inside of the supporting table 70 and rotatably supporting the catheter main body and a distal support portion 72 for rotatably supporting the core 62. The distal support portion 72 may rotatably support a distal portion of the catheter main body 20 instead of the core 62, if possible.

The moving mechanism section 80 includes a moving table 81 capable of moving linearly in a direction parallel to the axis of the balloon 30 and a tube fixing section 83 fixing the dispensing tube 94. The moving table 81 can move linearly by the driving source such as a motor built in the moving table 81. The tube fixing section 83 fixes an upper end of the dispensing tube 94 to the moving table 81. Therefore, the moving table 81 is moved, thereby moving the dispensing tube 94 linearly in the direction parallel to the axis of the balloon 30. In addition, the applying mechanism section 90 is placed on the moving table 81 and the applying mechanism section 90 is moved linearly in both directions along the axis.

The applying mechanism section 90 is a part in which the coating solution is applied to the surface of the balloon 30. The applying mechanism section 90 includes a container 92 storing the coating solution, a liquid delivering pump 93 feeding the coating solution at any feeding amount, and the dispensing tube 94 applying the coating solution to the balloon 30.

The liquid delivering pump 93 can be a syringe pump, for example, controlled by the control unit 99, which is configured to suction (or suck) the coating solution from the container 92 through a suction tube 91, and thus can supply the coating solution to the dispensing tube 94 through a supply tube 96 at any feeding amount. The liquid delivering pump 93 is placed on the moving table 81 and can move linearly by the movement of the moving table 81. The liquid delivering pump 93 is not limited to a syringe pump as long as the liquid delivering pump can feed the coating solution, and may be, for example, a tube pump.

The dispensing tube 94 is a member for communicating with the supply tube 96 and ejecting the coating solution supplied from the liquid delivering pump 93 through the supply tube 96 to the surface of the balloon 30. The dispensing tube 94 can be a cylindrical member having flexibility. The dispensing tube 94 has an opening portion 95 fixed to the upper end of the tube fixing section 83, extending vertically downward from the tube fixing section 83, and formed in an ejecting end 97 which is a lower end. The dispensing tube 94 moves the moving table 81, such that it is possible to move linearly in both directions along the axial direction of the balloon catheter 10 together with the liquid delivering pump 93 placed on the moving table 81. The dispensing tube 94 can supply the coating solution to the surface of the balloon 30 in a state where the dispensing tube is pressed against the balloon 30 and bent.

The dispensing tube 94 may be a cylindrical shape as long as the coating solution is supplied. In addition, the dispensing tube 94 may not extend in the vertical direction as long as the coating solution is ejected from the opening portion 95.

In accordance with an exemplary embodiment, it can be preferable that the dispensing tube 94 is formed of a flexible material so that a contact load in contact with the balloon 30 can be reduced and change in a contact position in accordance with the rotation of the balloon 30 can be absorbed by bending. Examples of a constituent material of the dispensing tube 94 can include, but are not limited to, polyolefins such as polyethylene, polypropylene, and the like, cyclic polyolefins, polyesters, polyamides, polyurethanes, and fluororesins such as polytetrafluoroethylene (PTFE), tetrafluoroethylene-ethylene copolymer (ETFE), tetrafluoroethylene-perfluoroalkylvinyl ether copolymer (PFA), tetrafluoroethylene-hexafluoropropylene copolymer (FEP), and the like. The constituent material is not limited as long as the constituent material is flexible and deformable.

An outer diameter of the dispensing tube 94 is not limited, and the outer diameter of the dispensing tube 94 can be, for example, 0.1 mm to 5.0 mm. An inner diameter of the dispensing tube 94 is not limited, and the inner diameter of the dispensing tube 94, can be, for example, 0.05 mm to 3.0 mm. A length of the dispensing tube 94 is not limited, and the length of the dispensing tube 94, may be a length five times or less the diameter of the balloon. For example, the length of the dispensing tube 94 can be, for example, from 1.0 mm to 50 mm.

The control unit 99 is composed of, for example, a computer, and generally controls the rotating mechanism section 61, the moving mechanism section 80, and the applying mechanism section 90. Therefore, the control unit 99 can generally control a rotational speed of the balloon 30, a moving speed of the dispensing tube 94 to the axial direction with respect to the balloon 30, and an ejecting rate of the drug from the dispensing tube 94, and other parameters.

The coating solution supplied to the balloon 30 by the dispensing tube 94 is a solution or a suspension containing the constituent material of the drug coating layer 40 and contains a water-insoluble drug, an additive (diluting agent), an organic solvent, and water. After the coating solution is supplied to the surface of the balloon 30, an organic solvent and water are volatilized, and thus the drug coating layer 40 having the plurality of elongated bodies 42 which are crystals of the water-insoluble drug and each have an independent long axis is formed on the surface of the balloon 30.

Viscosity of the coating solution can be, for example, 0.5 cP to 1500 cP, preferably 1.0 cP to 500 cP, and more preferably 1.5 cP to 100 cP.

The water-insoluble drug means a drug which is insoluble or relatively insoluble in water. In an aspect, the solubility of the water-insoluble drug in water, for example, is less than 1 mg/mL at pH 5 to 8. In certain embodiments, the solubility of the water-insoluble drug may be less than 0.1 mg/mL. In certain embodiments, the water-insoluble drug includes one or more fat-soluble drugs.

Some preferred examples of the water-insoluble drug include immunosuppressive drugs such as cyclosporines including cyclosporine, immunoactive drugs such as rapamycin, anticancer drugs such as paclitaxel, an antiviral drug or an antibacterial drug, an antineoplastic tissue drug, an analgesic drug and an antiinflammatory drug, an antibiotic drug, an antiepileptic drug, an anxiolytic drug, an antiparalysis drug, an antagonist, a neuron blocking drug, an anticholinergic drug and a cholinergic drug, an antimuscarinic drug and a muscarinic drug, an antiadrenergic drug, an antiarrhythmic drug, an antihypertensive drug, a hormone drug, and a nutritional supplement.

In accordance with certain embodiments, the water-insoluble drug may be preferably at least one selected from the group consisting of rapamycin, paclitaxel, docetaxel, and everolimus. The rapamycin, paclitaxel, docetaxel, and everolimus described above include their analogs and/or derivatives as long as the analogs and/or derivatives have equivalent drug activity to the original. For example, paclitaxel and docetaxel are in an analog relation. Rapamycin and everolimus are in a derivative relation. Among them, paclitaxel is more preferable.

The additive constitutes the additive layer 41 on the balloon 30. The additive contains a water-soluble low molecular weight compound. A molecular weight of the water-soluble low molecular weight compound is 50 to 2000, preferably 50 to 1000, more preferably 50 to 500, and still more preferably 50 to 200. An amount of the water-soluble low molecular weight compound can be, for example, preferably 10 parts by mass to 5000 parts by mass, more preferably 50 parts by mass to 3000 parts by mass, and still more preferably 100 parts by mass to 1000 parts by mass with respect to 100 parts by mass of the water-insoluble drug. Examples of a material of the water-soluble low molecular weight compound include serine ethyl ester, saccharides such as glucose, sugar alcohols such as sorbitol, citrate ester, polysorbate, polyethylene glycol, a water-soluble polymer, a contrast agent, amino acid ester, glycerol esters of a short-chain monocarboxylic acid, a pharmaceutically acceptable salt, a surfactant, and any mixture of two or more of them. The water-soluble low molecular weight compound is characterized by having a hydrophilic group and a hydrophobic group and being dissolved in water. The water-soluble low molecular weight compound is preferably a non-swelling water-soluble low molecular weight compound or hardly swelling water-soluble low molecular weight compound. The additive containing the water-soluble low molecular weight compound is effective to uniformly disperse the water-insoluble drug on the surface of the balloon 30. In accordance with an exemplary embodiment, it can be preferable that the additive constituting the additive layer 41 is not hydrogel. The additive layer 41 contains a low molecular weight compound, to thereby rapidly dissolve the additive layer without inflating when the additive layer is in contact with an aqueous solution. Furthermore, the additive layer 41 is easily dissolved at the time of inflating the balloon 30 in the blood vessel, such that an effect of easily releasing crystal particles of the water-insoluble drug on the surface of the balloon 30 and increasing an adhesive amount of the drug crystal particles to the blood vessel, is provided. In a case where the additive layer 41 is a matrix formed of a contrast agent such as Ultravist (registered trademark), the crystal particles are embedded in the matrix, and the crystals are not produced to extend from the balloon 30 toward outside of the matrix. Accordingly, the elongated body 42 in the present embodiment extends from the surface of the balloon 30 toward the surface of the additive layer 41.

The water-soluble low molecular weight compound has a molecular weight of 50 to 2000, and is dissolved at an amount of 1 mg/mL or more in water, preferably dissolved at an amount of 5 mg/mL or more in water, more preferably dissolved at an amount of 10 mg/mL or more in water, still more preferably dissolved at an amount of 33 mg/mL or more in water, and preferably dissolved in water without inflating. In accordance with an exemplary embodiment, it can be preferable that the water-soluble low molecular weight compound is not hydrogel. It is preferable that the water-soluble low molecular weight compound is not a polymer and a water-insoluble polymer. It is preferable that the water-soluble low molecular weight compound is not polyethylene glycol (PEG) and water-soluble PEG (for example, polyethylene glycol 200-600).

The solubility of a substance can be defined as a degree of dissolution within 30 minutes at 20° C. For example, the solubility of substance can be defined by an amount of solvent (for example, an amount of water) required to dissolve 1 g (or 1 mL) of solute. In cases where the amount of solvent required to dissolve 1 g of solute is less than 1 mL, the solute may be regarded as extremely soluble in the solvent. In cases of extremely soluble solutes, the amount of dissolved solute is more than 1000 mg/m L. Examples of extremely soluble substances include sorbitol, urea, and glycerol. In cases where the amount of solvent required to dissolve 1 g of solute is 1 mL or more and less than 10 mL, the solute may be regarded as soluble in the solvent. In cases, of soluble solutes, the amount of dissolved solute may be more than 100 mg/mL and 1000 mg/mL or less. Examples of soluble substances include polysorbate, amino acid ester, polyethylene glycol 200-600, serine ethyl ester, a contrast agent (iopromide), and a water-soluble polymer. In cases where the amount of solvent required to dissolve 1 g of solute is 10 mL or more and less than 30 mL, the solute may be regarded as slightly soluble in the solvent. In cases of slightly soluble solutes, the amount of dissolved solute may be more than 33 mg/mL and 100 mg/mL or less. Examples of slightly soluble substances include polyethylene glycol. In cases where the amount of solvent required to dissolve 1 g of solute is 30 mL or more and less than 100 mL, the solute may be regarded as sparingly soluble in the solvent. In cases of sparingly soluble solutes, the amount of dissolved solute may be more than 10 mg/mL and 33 mg/mL or less. In cases where the amount of solvent required to dissolve 1 g of solute is 100 mL or more and less than 1000 mL, the solute may be regarded as insoluble in the solvent. In cases of insoluble solutes, the amount of dissolved solute may be more than 1 mg/mL and 10 mg/mL or less. In cases where the amount of solvent required to dissolve 1 g of solute is 1000 mL or more and less than 10000 mL, the solute may be regarded as extremely insoluble in the solvent. In cases of extremely insoluble solutes, the amount of dissolved solute may be more than 0.1 mg/mL and 1 mg/mL or less. In cases where the amount of solvent required to dissolve 1 g of solute is 10000 mL or more, the solute may be regarded as relatively insoluble (i.e., hardly soluble solutes) in the solvent. In cases of relatively insoluble solutes, the amount of dissolved solute may be is 0.1 mg/mL or less. Examples of relatively insoluble substances include fatty acid ester of glycerol. The water-soluble substance may be a substance other than a substance which is "extremely insoluble", or a substance which is "hardly soluble", and "relatively insoluble". Specifically, the water-soluble substance may be selected from substances which are "extremely soluble", "soluble", "sparingly soluble" or "insoluble". In certain embodiments, the water-soluble substance may be selected from substances which are "extremely soluble", "soluble", and "sparingly soluble".

The organic solvent is not particularly limited, and examples of the organic solvent can include tetrahydrofuran, acetone, glycerin, ethanol, methanol, dichloromethane, hexane, and ethyl acetate. In certain embodiments, the organic solvent is a mixture of some tetrahydrofuran, ethanol, and acetone.

Suitable mixtures of the organic solvent and water include, but are not limited to, a mixture of tetrahydrofuran and water, a mixture of tetrahydrofuran, ethanol, and water, a mixture of tetrahydrofuran, acetone, and water, a mixture of acetone, ethanol, and water, and a mixture of tetrahydrofuran, acetone, ethanol, and water.

Next, a method for forming crystals of the water-insoluble drug on the surface of a balloon 30 using the above-described balloon coating apparatus 60 will be described.

First, inflation fluid is supplied to the balloon 30 through the three-way stopcock which is connected to the proximal opening portion 27 of the balloon catheter 10. Next, the three-way stopcock is operated to seal the inflation lumen 23 in a state in which the balloon 30 is inflated and maintains the state in which the balloon 30 is inflated. The balloon 30 is inflated in a pressure (for example, 4 atmosphere) lower than a pressure (for example, 8 atmosphere) at the time of using the balloon in the blood vessel. The drug coating layer 40 can be formed on the surface of the balloon 30 without inflating the balloon 30, and in this case, it is not required to supply the inflation fluid to the balloon 30.

Next, the balloon catheter 10 is rotatably placed on the supporting table 70 in a state in which the dispensing tube 94 is not in contact with the surface of the balloon 30 and the hub 26 is interlocked with the rotating mechanism section 61.

Next, a position of the moving table 81 is adjusted to position the dispensing tube 94 to the balloon 30. Here, the dispensing tube 94 is positioned at the most distal side of the balloon 30 on which the drug coating layer 40 is formed. As an example, an extending direction (ejecting direction) of the dispensing tube 94 is a direction opposite to a rotation direction of the balloon 30. Therefore, the balloon 30 can be rotated only in a direction opposite to a direction in which the coating solution is ejected from the dispensing tube 94 at a position where the balloon comes into contact with the dispensing tube 94. This rotation in the direction opposite to the ejecting direction gives a physical stimulus to the coating solution, thereby promoting the formation of crystal nuclei of the drug crystal. The extending direction (ejecting direction) toward the opening portion 95 of the dispensing tube 94 is a direction opposite to a rotation direction of the balloon 30, such that the crystals of the water-insoluble drug formed on the surface of the balloon 30 are likely to be formed by including a morphological form which includes the plurality of elongated bodies 42 and each have an independent long axis. The extending direction of the dispensing tube 94 may not be the direction opposite to the rotation direction of the balloon 30. Thus, the extending direction of the dispensing tube can be the same as the direction opposite to the rotation direction of the balloon or a direction perpendicular to the surface of the balloon 30.

Next, the coating solution is supplied to the dispensing tube 94 while adjusting the feeding amount by the liquid delivering pump 93, and the balloon catheter 10 is rotated by the rotating mechanism section 61. Furthermore, the moving table 81 is moved, thereby gradually moving the dispensing tube 94 to a proximal direction along the axial direction of the balloon 30. The dispensing tube 94 is moved relatively to the balloon 30, such that the coating solution ejected from the opening portion 95 of the dispensing tube 94 is applied to an outer circumferential surface of the balloon 30 while drawing a spiral.

In accordance with an exemplary embodiment, the moving speed of the dispensing tube 94 is not particularly limited, and the moving speed of the dispensing tube 94 can be, for example, 0.01 mm/sec to 2 mm/sec, preferably 0.03 mm/sec to 1.5 mm/sec, and more preferably 0.05 mm/sec to 1.0 mm/sec. The ejecting speed of the coating solution from the dispensing tube 94 is not particularly limited, and for example, the ejecting speed of the coating solution from the dispensing tube 94 can be, for example, 0.01 μL/sec to 1.5 μL/sec, preferably 0.01 μL/sec to 1.0 μL/sec, and more preferably 0.03 μL/sec to 0.8 μL/sec. The rotational speed of the balloon 30 is not particularly limited, and for example, the rotational speed of the balloon can be, 10 rpm to 300 rpm, preferably 30 rpm to 250 rpm, and more preferably 50 rpm to 200 rpm. The diameter of the balloon 30 at the time of applying the coating solution is not particularly limited, and for example, the diameter of the balloon 30 at the time of applying the coating solution can be 1 mm to 10 mm and preferably 2 mm to 7 mm.

Figure 10:
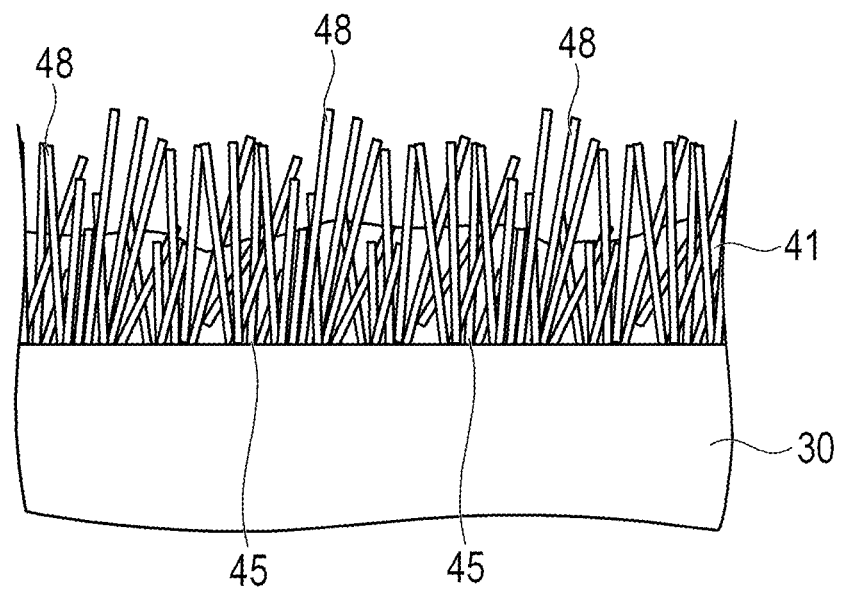
FIG. 10 is a cross-sectional view of the surface of the balloon on which elongated drug crystals are formed.

Thereafter, the organic solvent containing the coating solution which is applied to the surface of the balloon 30 is volatilized earlier than water. Therefore, the organic solvent is volatilized in a state in which the water-insoluble drug, the water-soluble low molecular weight compound, and water remain on the surface of the balloon 30. As such, when the organic solvent is volatilized in a state in which water remains, the water-insoluble drug is precipitated in the water-soluble low molecular weight compound containing water, the crystals gradually grow from crystal nuclei, and as illustrated in FIG. 10, the morphological drug crystals including the plurality of protruding crystals 48 in which the crystals each have an independent long axis are formed on the surface of the balloon 30. After the organic solvent is volatilized and the drug crystals are precipitated as the plurality of protruding crystals 48, water evaporates more slowly than the organic solvent, and the additive layer 41 containing the water-soluble low molecular weight compound is thus formed. In accordance with an exemplary embodiment, a time when water evaporates can be appropriately set depending on a type of drug, a type of water-soluble low molecular weight compound, a type of organic solvent, a ratio of material, an amount of application of the coating solution, and the like, and for example, the time when the water evaporates can be about 1 seconds to 600 seconds. A length of a part of the protruding crystal 48 protruding from the surface of the additive layer 41 toward the outside is not limited, and for example, the length of the part of the protruding crystal 48 protruding from the surface of the additive layer 41 toward the outside can be more than 1 μm and 10 μm or less. The protruding crystal 48 is embedded in the additive layer 41 at a length of equal to or longer than half of the total length of the protruding crystal 48. The drug crystal (elongated body 42) which has no exposed portion embedded in the additive layer 41 can also exist.

By moving the dispensing tube 94 to the axial direction of the balloon 30 while rotating the balloon 30, the drug coating layer 40 is gradually formed on the surface of the balloon 30 toward the axial direction. After the drug coating layer including the protruding crystal 48 and the additive layer 41 is entirely formed in the range of the balloon 30 to be coated, the rotating mechanism section 61, the moving mechanism section 80, and the applying mechanism section 90 are stopped.

Thereafter, the balloon catheter 10 is separated from the balloon coating apparatus 60 and completes the coating of the balloon 30.

Next, a balloon folding apparatus will be described. The balloon folding apparatus is an apparatus capable of folding the balloon 30 so as to be wound around the inner tube 22.

Figure 6:
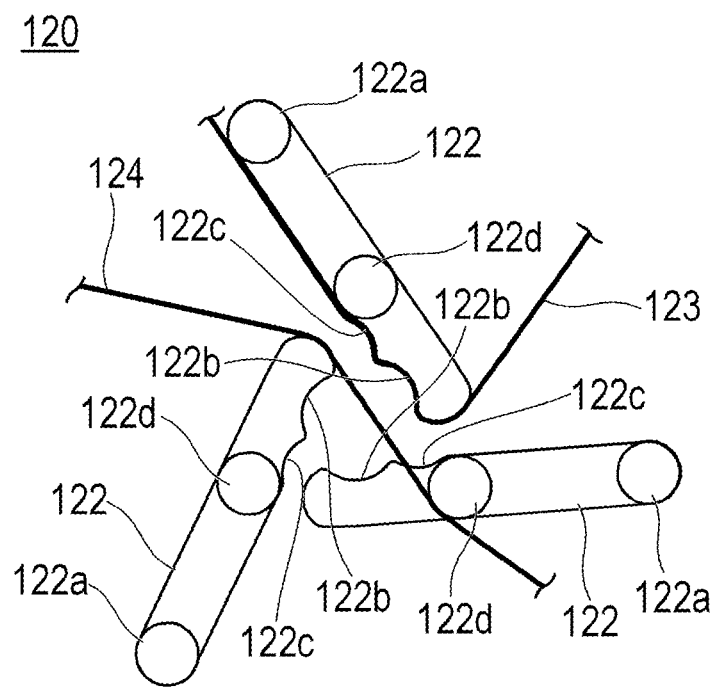
FIG. 6 is a front view illustrating blades of a pleating section.
Figure 7:
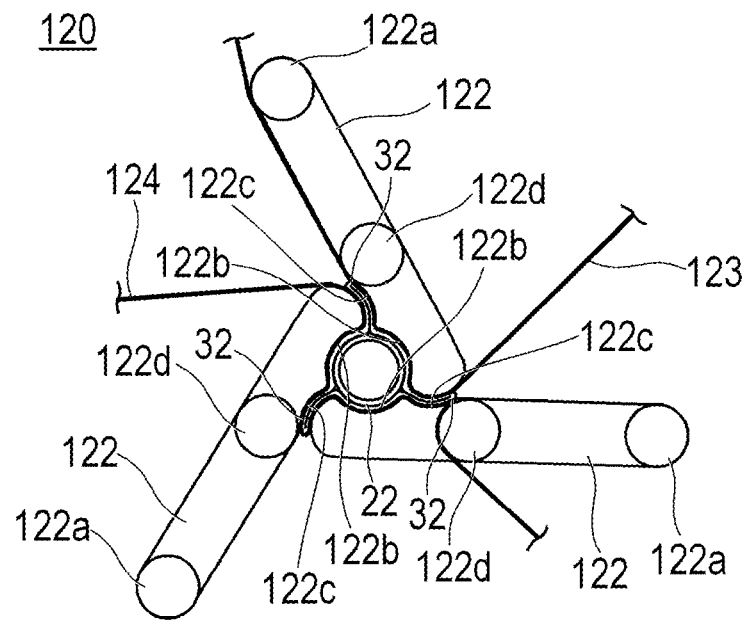
FIG. 7 is a front view illustrating a state in which the blades of the pleating section are rotated to form pleat portions on the balloon.
Figure 8:
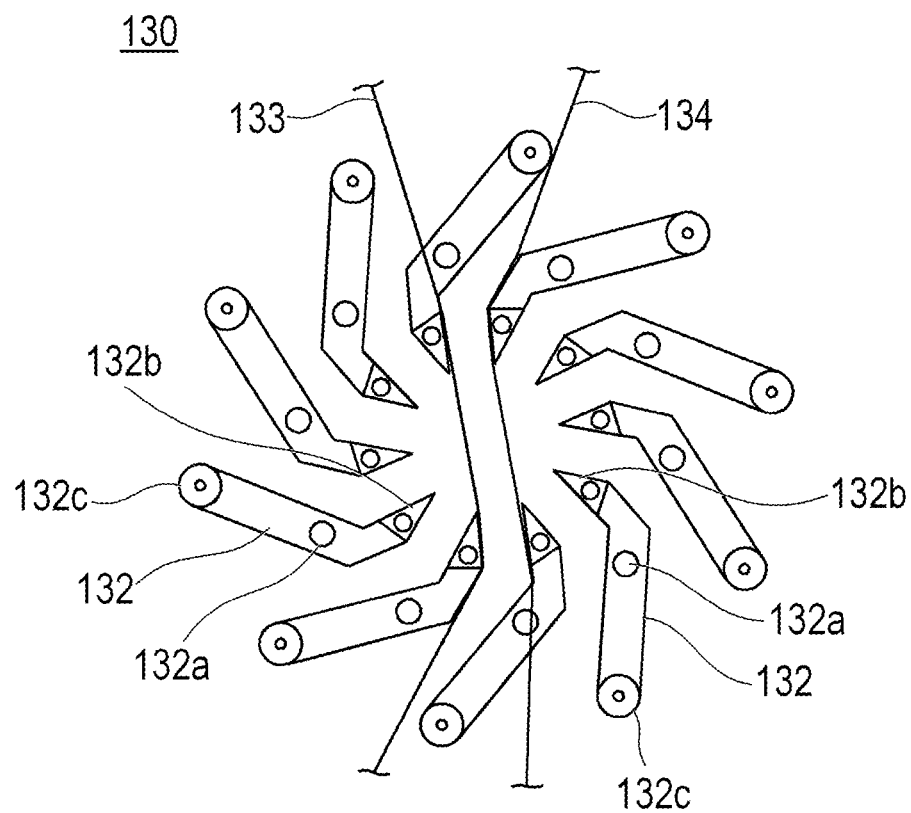
FIG. 8 is a front view illustrating blades of a folding section.
Figure 9:
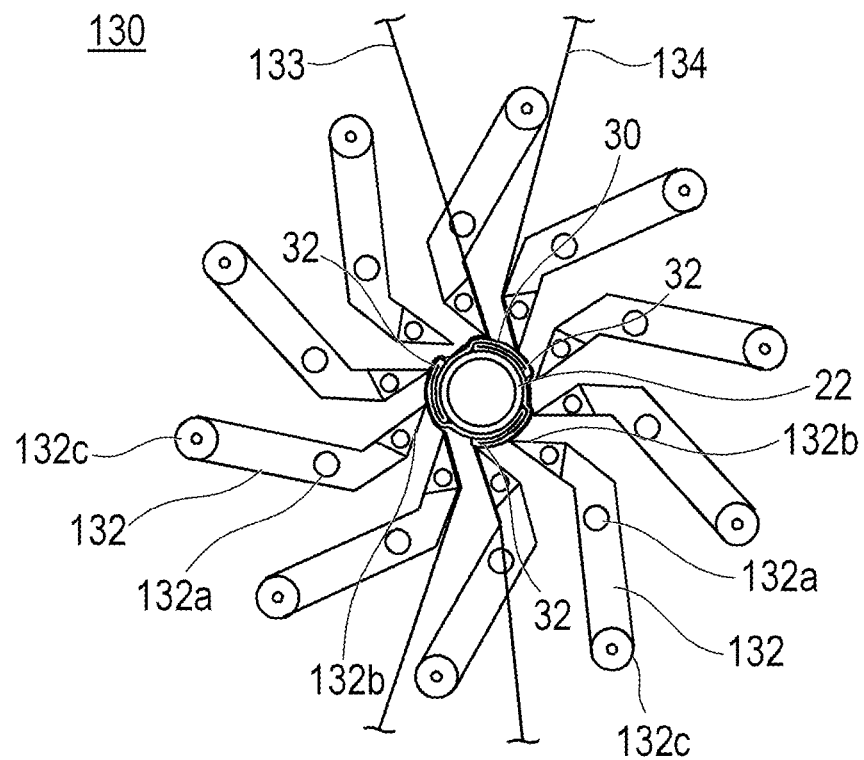
FIG. 9 is a front view illustrating a state in which the blades of the folding section are rotated to fold the pleat portions of the balloon.
Figure 12:
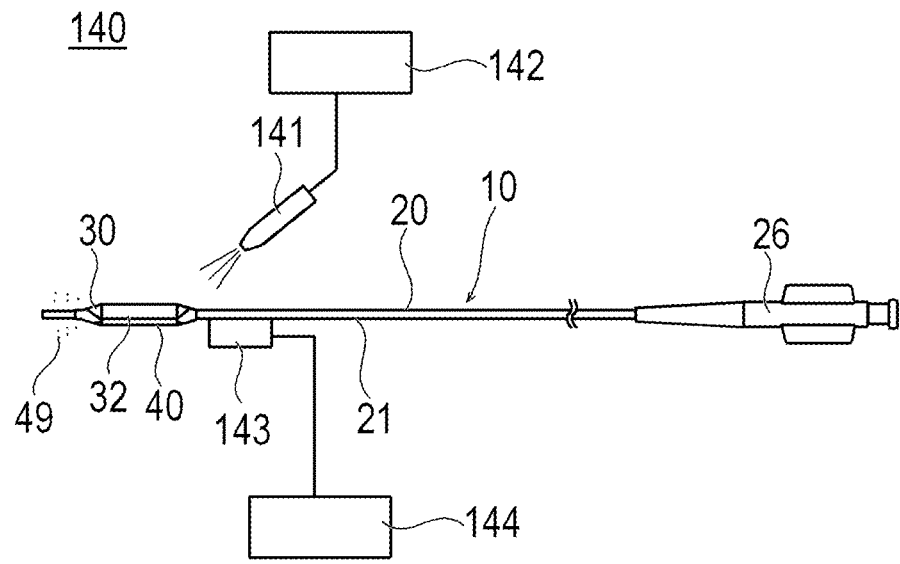
FIG. 12 is a front view illustrating a removal section.

The balloon folding apparatus includes a pleating section 120 illustrated in FIG. 6, a folding section 130 illustrated in FIG. 8, and a removal section 140 illustrated in FIG. 12. In the pleating section 120, a pleat portion (i.e., pleat) 32 protruding in the radial direction is formed in the balloon 30 as illustrated in FIG. 7. In the folding section 130, the pleat portion 32 formed in the balloon 30 can be folded by laying the pleat portion in a circumferential direction as illustrated in FIG. 9. The pleat portion 32 formed in the balloon 30 is formed due to a fold extending the balloon 30 in a substantially axial direction, and when viewed in a cross section perpendicular to the axis of the balloon 30, the fold is formed so as to protrude from the long axis of the balloon 30 to the circumferential direction. In accordance with an exemplary embodiment, a length of the pleat portion 32 in the long axial direction does not exceed a length of the balloon 30. The length of the pleat portion 32 in a direction in which the pleat portion protrudes from the catheter main body 20 in the circumferential direction, can be, for example, about 1 mm to 8 mm. The number of pleat portions 32 is not particularly limited, and the number of pleat portions 32 can be, for example, 2 to 7, but in the present embodiment, the number of pleat portions is 3. As illustrated in FIG. 12, the removal section 140 can remove the extra drug crystals from the balloon 30.

First, a pleating section 120 will be described. As illustrated in FIGS. 6 and 7, the pleating section 120 has three blades 122 in the pleating section 120. Each of the blades 122 is a plate-shaped member in which a cross-sectional shape at each position of the balloon catheter 10 to be inserted along the axial direction is formed into the same shape. Each of the blades 122, for example, can be disposed to be 120 degrees with respect to a center position through which the balloon 30 is inserted. That is, each of the blades 122 is disposed in the circumferential direction at every equal angle. The blade 122 has a rotating center portion 122a in the vicinity of an outer circumferential end of the blade and can be rotated around the rotating center portion 122a. In addition, the blade 122 has a movable pin 122d provided on an inner circumferential side from the rotating center portion 122a and extending in the axial direction. The movable pin 122d can be movable around the rotating center portion 122a. When the movable pin 122d is moved, each of the blades 122 is rotated around the rotating center portion 122a. The three blades 122 are rotated, such that a spatial region of the center portion surrounded by the blade 122 can be narrowed. Note that, the number of blades 122 is not particularly limited as long as the number of blades is 2 or more.

The blade 122 has a substantially arc-shaped first shape forming section 122b and a substantially arc-shaped second shape forming section 122c on an inner circumferential end opposite to the rotating center portion 122a. The first shape forming section 122b is attached to the surface of the balloon 30 into which the pleating section 120 is inserted in accordance with the rotation of the blade 122, such that the pleat portion 32 protruding in the radial direction can be formed in the balloon 30. The second shape forming section 122c is attached to a part of the pleat portion formed in the balloon 30 in accordance with the rotation of the blade 122, such that the pleat portion 32 can be curved in a predetermined direction. In addition, the pleating section 120 has a heater (not illustrated) for heating the blades 122.

In the blade 122, a first film 123 and a second film 124 which are made of a resin are supplied so as to flow in one direction. The first film 123 is coupled to a surface of the blade 122 disposed at an upper portion of the pleating section. The second film 124 is coupled to other two blades 122 disposed at a lower portion of the pleating section. Accordingly, the center position of the pleating section 120 through which the balloon 30 is inserted is surrounded by the first film 123 and the second film 124.

When the balloon 30 is inserted into the pleating section 120 and the blade 122 is rotated to form the pleat portion 32 in the balloon 30, the first film 123 and the second film 124 protect so that the balloon 30 does not directly come into contact with the surface of the blade 122. After the pleat portion 32 of the balloon 30 is formed, the first film 123 and the second film 124 are moved by a predetermined length. That is, a part in which the first film 123 and the second film 124 come into contact with the balloon 30 once does not come into contact with the balloon 30 again, and a new part is supplied to the center position of the pleating section 120 every time the balloon 30 is inserted.

First, the folding section 130 will be described. As illustrated in FIGS. 8 and 9, the folding section 130 has ten blades 132 in the folding section 130. Each of the blades 132 is a plate-shaped member in which a cross-sectional shape at each position of the balloon catheter 10 to be inserted along the axial direction is formed into the same shape. Each of the blades 132 can be, for example, disposed to be 36 degrees with respect to a center position through which the balloon is inserted. That is, each of the blades 132 is disposed in the circumferential direction at equal angular intervals. Each blade 132 has a rotating center portion 132a in the vicinity of a substantial center of the blade and can be rotated around the rotating center portion 132a. In addition, each of the blades 132 has a movable pin 132c provided in the vicinity of a substantial outer circumferential end of the blade and extending in the axial direction. The movable pin 132c can be movable around the rotating center portion 132a. When the movable pin 132c is moved, each of the blades 132 is rotated around the rotating center portion 132a. The ten blades 132 are rotated, such that a spatial region of the center portion surrounded by the blade 132 can be narrowed. Note that, the number of blades 132 is not particularly limited to 10.

The blade 132 has a tip side being curved and a tip portion 132b has a relatively sharp shape. As the blade 132 rotates, the tip portion 132b comes into contact with the surface of the balloon 30 inserted into the folding section 130 so that the pleat portion 32 formed in the balloon 30 can be folded so as to be laid in the circumferential direction. In addition, the folding section 130 has a heater (not illustrated) for heating the blades 132.

In the folding section 130, a third film 133 and a fourth film 134 which are made of a resin are supplied so as to flow in one direction. The third film 133 and the fourth film 134 are disposed to face each other, such that the third film and the fourth film sandwich a central spatial region surrounded by the blades 132. When the balloon 30 is inserted into the folding section 130, the third film 133 and the fourth film 134 protect so that the balloon 30 does not directly come into contact with the surface of the blade 132.

First, the removal section 140 will be described. As illustrated in FIG. 12, the removal section 140 includes a gas supply section 141 which is a nozzle for releasing gas and a vibrating section 143 for vibrating the balloon 30. The gas supply section 141 releases gas supplied from a gas supply section 142 to the balloon 30. The released gas can be, for example, helium gas, $CO_2$ gas, $O_2$ gas, $N_2$ gas, Ar gas, air, and mixed gas. The vibrating section 143 vibrates the balloon 30 by current supplied from a vibrating device 144. For example, the vibrating section 143 can vibrate the balloon 30 through the outer tube 21. A position where the vibrating section 143 comes into contact with the balloon catheter 10 is not particularly limited as long as the balloon 30 is vibrated.

Next, a method for folding the balloon 30, in which the drug coating layer is formed on the surface by the balloon coating apparatus 60 using the balloon folding apparatus, will be described.

First, in order to form the pleat portions 32 in the balloon 30, the balloon 30 of the balloon catheter 10 is inserted into the pleating section 120 illustrated in FIG. 6. The blades 122 of the pleating section 120 are heated. Next, as illustrated in FIG. 7, the blades 122 are rotated. As a result, the first shape forming section 122b of each of the blades 122 approaches, and a center region between the blades 122 is thus narrowed. According to this, the balloon 30 inserted into the center region between the blades 122 is pressed against the inner tube 22 by the first shape forming section 122b. A part of the balloon 30 which is not pressed by the first shape forming section 122b is pushed out to a clearance between the tip portion of the blade 122 and the second shape forming section 122c of the blade 122 adjacent to the corresponding blade 122, and the pleat portion 32 curved in one side is thus formed. Since the balloon 30 is heated to about 50 degrees Celsius (° C.) to 60 degrees Celsius (° C.) by the blade 122, the formed pleat portions 32 can maintain their shape. Thus, the three pleat portions 32 in the circumferential direction are formed in the balloon 30.

In this case, the surface coming into contact with the balloon 30 of each of the blades 122 is covered with the first film 123 and the second film 124, such that the balloon 30 does not directly come into contact with the surface of the blade 122. After the pleat portion 32 is formed in the balloon 30, the blade 122 is rotated so as to return to its original position, and the balloon 30 is withdrawn from the pleating section 120. In a pleating process, since a volume inside the balloon 30 is reduced, it is preferable that the three-way stopcock is adjusted in accordance with the reduction of the volume and the inflation fluid is discharged to the outside to deflate the balloon 30. Thus, it is possible to prevent the excessive force from being applied to the balloon 30.

Figure 11:
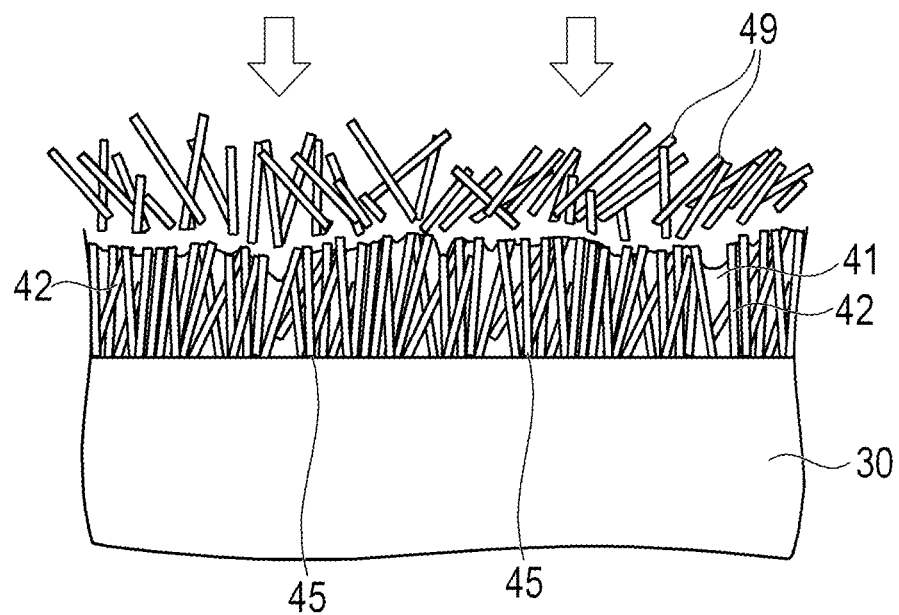
FIG. 11 is a cross-sectional view of the surface of the balloon in a state in which a surplus portion of the elongated drug crystals is cut out.
Figure 13A:
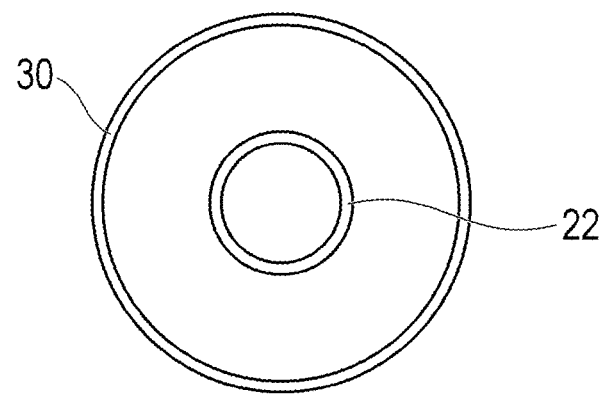
Figure 13B:
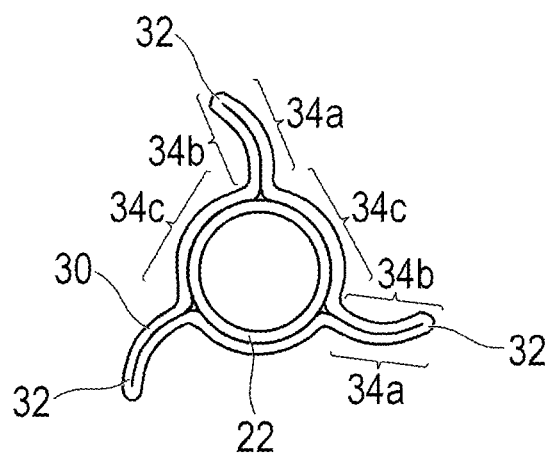

As illustrated in FIG. 13A, the balloon 30 has a cross section with a substantial circular shape in a state where the inflation fluid is injected inside the balloon. By forming the protruding pleat portion 32 from this state, as illustrated in FIG. 13B, the balloon 30 includes a blade outer portion 34a pressed against the second shape forming section 122c and constituting an outer surface of the pleat portion 32, a blade inner portion 34b pressed against the tip portion of the blade 122 and constituting an inner surface of the pleat portion 32, and an intermediate portion 34c located between the blade outer portion 34a and the blade inner portion 34b and pressed against the first shape forming section 122b. Then, the drug coating layer of the balloon 30 receives a pressing force from the first film 123 and the second film 124 which are pressed by the blade (pressing section) 122, and the drug coating layer is further heated. By using the pressing force and heat, as illustrated in FIG. 11, a part protruding from the additive layer 41 of the protruding crystal 48 is folded and the surplus portion 49 can be cut out. A part located inside the additive layer 41 of the protruding crystal 48 is protected by the additive layer 41, remains inside the additive layer 41, and thus becomes an elongated body 42. All the parts protruding from the additive layer 41 of the protruding crystal 48 do not need to be cut out.

Next, the balloon catheter 10 is withdrawn from the pleating section 120. Next, the balloon 30 of the balloon catheter 10 is inserted into the folding section 130 illustrated in FIG. 8. The blades 132 of the folding section 130 are heated to about 50 degrees Celsius to 60 degrees Celsius.

After the balloon 30 in which the pleat portions 32 are formed is inserted into the folding section 130, the blades 132 are rotated as illustrated in FIG. 9. As a result, the tip portion 132b of each of the blades 132 approaches to each other, and a center region between the blades 132 is thus narrowed. According to this, the balloon 30 inserted into the center region between the blades 132 is in a state in which the pleat portions 32 are laid in the circumferential direction by the tip portion 132b of each of the blades 132. Since the blade 132 is heated in advance before inserting the balloon 30 and the balloon 30 is heated by the blade 132, the pleat portion 32 which is laid in the circumferential direction can maintain its shape as it is by the blade 132. Here, the surface coming into contact with the balloon 30 of each of the blades 132 is covered with the third film 133 and the fourth film 134, such that the balloon 30 does not directly come into contact with the surface of the blade 132.

Figure 13C:
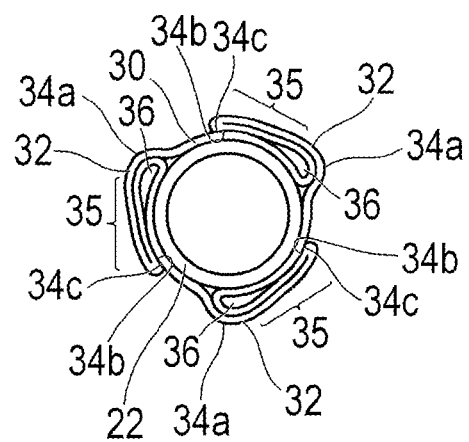

When the pleat portion 32 of the balloon 30 is folded, as illustrated in FIG. 13C, the blade inner portion 34b and the intermediate portion 34c come into contact with each other in an overlapped manner, and an overlapped portion 35 in which the surfaces of the balloon face and overlap each other is formed. Then, a part of the intermediate portion 34c and the blade outer portion 34a are exposed to the outside without covering the blade inner portion 34b. In addition, a root side space portion 36 is formed between a root portion of the pleat portion 32 and the intermediate portion 34c in a state in which the balloon 30 is folded. In a region of the root side space portion 36, a relatively small or minute clearance is formed between the pleat portion 32 and the intermediate portion 34c. On the other hand, a region of the tip side from the root side space portion 36 of the pleat portion 32 can be in contact with the intermediate portion 34c. The blade outer portion 34a of the balloon 30 receives a pressing force that a first film 181 and a second film 182 which are pressed by the blade (pressing section) 132 are rubbed in the circumferential direction, and the blade outer portion is further heated. By using the pressing force and heat, as illustrated in FIG. 11, a part protruding from the additive layer 41 of the protruding crystal 48 is folded and the surplus portion 49 can be cut out. A part located inside the additive layer 41 of the protruding crystal 48 is protected by the additive layer 41, remains inside the additive layer 41, and thus becomes an elongated body 42. All the parts protruding from the additive layer 41 of the protruding crystal 48 do not need to be cut out.

As described above, the protruding crystal 48 receives a force from the blades 122 of the pleating section 120 and the blades 132 of the folding section 130, and the surplus portion 49 is thus cut out. The surplus portion 49 may be cut out from the protruding crystal 48 by receiving a force from either the pleating section 120 or the folding section 130. The surplus portion 49 is cut out from the protruding crystal 48, thereby forming the drug coating layer 40 including the additive layer 41 and the elongated body 42 on the surface of the balloon 30.

After the pleat portions 32 of the balloon 30 are folded, the blades 132 are rotated so as to return to its original position. Next, the balloon 30 is withdrawn from the folding section 130. Thus, the folding of the balloon 30 is completed.

Next, the balloon catheter 10 is disposed in the removal section 140 illustrated in FIG. 12. Gas is released from the gas supply section 141 while vibrating the balloon 30 by the vibrating section 143. As a result, the surplus portion 49 attached to the drug coating layer 40 of the balloon 30 is separated from the drug coating layer 40 due to a vibration and blown away by the gas supplied from the gas supply section 141. The blown gas enters between the pleat portion 32 and the intermediate portion 34c (see FIG. 13C) and can blow away the surplus portion 49 between the pleat portion 32 and the intermediate portion 34c. Thus, the surplus portion 49 can be effectively removed from the balloon 30 and the drug coating layer 40.

A drug coating layer 40, from which the surplus section 49 is removed, includes the plurality of elongated bodies 42 which are crystals of the water-insoluble drug and each have a long axis extending from the surface of the balloon 30 at various lengths and angles, and a water-soluble additive layer 41 which is provided in a space between the outer surface 51 and the surface of the balloon 30 so as to fill the space between the elongated bodies 42, the outer surface 51 being located outside the aggregate 50 of the plurality of elongated bodies 42 and having an unevenness connecting a plurality of tip ends 46 and side surfaces 43 of the elongated bodies 42 to each other, in which the tip ends 46 of the elongated bodies 42 hardly (i.e., slightly) protrude from the additive layer 41, and the side surface 43 and/or the tip surface 47 of the elongated body 42 are exposed on the surface of the additive layer 41. The tip end 46 of the elongated body 42 can slightly protrude from the additive layer 41. In the drug coating layer 40, since the tip end of the elongated body 42 hardly (i.e., slightly) protrudes from the additive layer 41, the breakage of the elongated body 42 on the surface of the balloon 30 can be prevented and the elongated body 42 can be maintained in an appropriate shape in order to act on the living body.

Next, an effect of the drug coating layer 40 will be described.

As illustrated in FIG. 3, in the drug coating layer 40 on the surface of the balloon 30, the water-soluble additive layer 41 is provided so as to fill a space between the elongated bodies 42. That is, the additive layer 41 is embedded between the elongated bodies 42. The folded and cut-out surplus portion 49 of the drug crystal is removed by the removal section 140. Therefore, when the folded balloon 30 is inserted into the blood vessel, the surplus portion 49 can be prevented from flowing out in the blood. Thus, it is possible to prevent the surplus portion 49 from having an undesirable effect on the living body.

After the balloon 30 is disposed at the stenosed site, as illustrated in FIGS. 1 and 2, the inflation fluid from the proximal opening portion 27 of the hub 26 is injected in a predetermined amount using an inflator, a syringe, or the like, and the inflation fluid is fed into the balloon 30 through the inflation lumen 23. Thus, the folded balloon 30 is inflated. Consequently, the drug coating layer 40 provided on the surface of the balloon 30 comes into contact with the stenosed site. When the drug coating layer 40 is pressed against to a biological tissue, the drug is delivered to the living body while dissolving the additive layer 41 which is the water-soluble low molecular weight compound contained in the drug coating layer 40. In addition, when the balloon 30 is inflated, cracks are generated in the additive layer 41 and the additive layer is rather easily thus dissolved, and the elongated bodies 42 which are the drug crystals are rather easily released from the additive layer 41.

When the inflation fluid is sucked from the proximal opening portion 27 of the hub 26 and discharged from the inside of the balloon 30, the balloon 30 is deflated and folded. Thus, the balloon catheter 10 can be extracted from the blood vessel.

As described above, the method for forming the drug coating layer 40 according to an embodiment is a method for forming the drug coating layer 40 in which the plurality of elongated bodies 42 which are crystals of the water-insoluble drug and each have a long axis are formed on the surface of the balloon 30, and the method includes supplying the coating solution which contains the water-insoluble drug, the water-soluble additive, the organic solvent, and water to the surface of the balloon 30 and evaporating the organic solvent and the water to form the additive layer 41 containing the water-soluble additive and the protruding crystal 48 having the tip end protruding from the additive layer, cutting out the surplus portion 49 protruding from the additive layer 41 of the protruding crystal 48 from a part surrounded by the additive layer 41 and forming the part surrounded by the additive layer 41 as the elongated body 42, and removing the cut-out surplus portion 49 from the drug coating layer 40.

In the method for forming the drug coating layer 40 as described above, since the surplus portion 49 protruding from the additive layer 41 of the protruding crystal 48 is removed, the elongated body 42 which is surrounded by the additive layer 41 and is a drug crystal can be obtained that is not easily broken. Therefore, it is possible to prevent the breakage of the elongated body 42 on the surface of the balloon 30 and maintain the elongated body 42 in an appropriated shape in order to act on the living body. In order to remove the surplus portion 49, the surplus portion 49 can be prevented from flowing out in the blood when the folded balloon 30 is inserted into the blood vessel. Thus, it is possible to prevent the surplus portion 49 from having an undesirable effect on the living body. Furthermore, since the side surface 43 and/or the tip surface 47 of the elongated body 42 is exposed on the surface of the additive layer 41, the additive layer 41 does not interfere with transferability in blood vessel of the elongated body 42 which is a drug, without excessively embedding the elongated body 42 in the additive layer 41.

The additive in the additive layer 41 protects the drug crystals while moving in the blood vessel. Alternatively, when the balloon 30 is inflated in a target lesion, the additive layer 41 for protecting the crystals in a product package form comes into contact with the blood, such that the additive is rapidly dissolved. As a result, an effect that the drug crystals come into contact with a blood vessel wall is shown.

In addition, the additive layer 41 contains a water-soluble low molecular weight compound. Thus, the additive layer 41 is rapidly dissolved in the blood vessel, and thus does not interfere with the transferability in blood vessel of the elongated body 42 which is a drug.

In addition, in the removing the surplus portion 49, the surplus portion 49 is removed from the drug coating layer 40 by blowing gas to the surface of the balloon 30. Thus, it is possible to prevent the surplus portion 49 separated from the elongated body 42 from being affected to the living body by entering the living body without remaining the surplus portion on the balloon 30.

In addition, in the removing the surplus portion 49, the surplus portion 49 may be removed from the drug coating layer 40 by applying vibration to the surface of the balloon 30. Thus, it is possible to prevent the surplus portion 49 separated from the elongated body 42 from being affected to the living body by entering the living body without remaining the surplus portion on the balloon 30.

In addition, the removing the surplus portion 49 includes forming the pleat portion 32 protruding outward in the radial direction of the balloon 30 after the protruding crystal 48 is formed, and folding the pleat portion 32 along the circumferential direction of the balloon 30. In at least one of the forming of the pleat portion 32 and the folding of the pleat portion 32, a force is applied to the surplus portion 49 protruding from the additive layer 41 of the protruding crystal 48, and the surplus portion 49 is thus be cut out from the elongated body 42. Thus, in the process of folding the balloon 30, the surplus portion 49 of the drug crystal can be effectively removed.

The water-insoluble drug contains at least one selected from the group consisting of rapamycin, paclitaxel, docetaxel, and everolimus. Thus, it is possible to properly prevent restenosis of the stenosed site in the blood vessel due to the elongated body 42 which is a drug crystal.

An apparatus for forming the drug coating layer 40 according to the present embodiment is an apparatus for forming the drug coating layer 40 in which the plurality of elongated bodies 42 which are crystals of the water-insoluble drug crystal and each have a long axis is formed on the surface of the balloon 30, and the apparatus includes the rotating mechanism section 61 applying a rotational force to the balloon 30, the dispensing tube (coating solution supply section) 94 applying the coating solution which contains the water-insoluble drug, the water-soluble additive, the organic solvent, and water to the surface of the rotating balloon 30, the blades (pressing sections) 122 and 132 pressing the surface of the balloon 30 and breaking a part of the protruding crystal 48 formed on the surface of the balloon 30, and a gas supply section 141 removing the broken surplus portion 49 by blowing gas to the surface of the balloon 30.

In addition, in the apparatus for forming a drug coating layer 40 as described above, a part of the drug crystal formed on the surface of the balloon 30 can be cut out by the blades (pressing sections) 122 and 132, and thus the cut-out surplus portion 49 can be removed by the gas supply section 141. Thus, it is possible to prevent the surplus portion 49 separated from the elongated body 42 from being affected to the living body by entering the living body without remaining the surplus portion on the balloon 30.

The forming apparatus further includes a vibrating section 143 for vibrating the balloon 30. Thus, the cut-out surplus portion 49 can be removed due to the vibration. Thus, it is possible to prevent the surplus portion 49 separated from the elongated body 42 from being affected to the living body by entering the living body without remaining the surplus portion 49 on the balloon 30.

The present disclosure is not limited only to the aforementioned embodiment, and various modifications can be made by a person skilled in the art within the technical thought of the present disclosure. For example, the balloon catheter 10 according to the above-described embodiment may be a rapid exchange type balloon catheter or an over-the-wire type balloon catheter.

Figure 14:
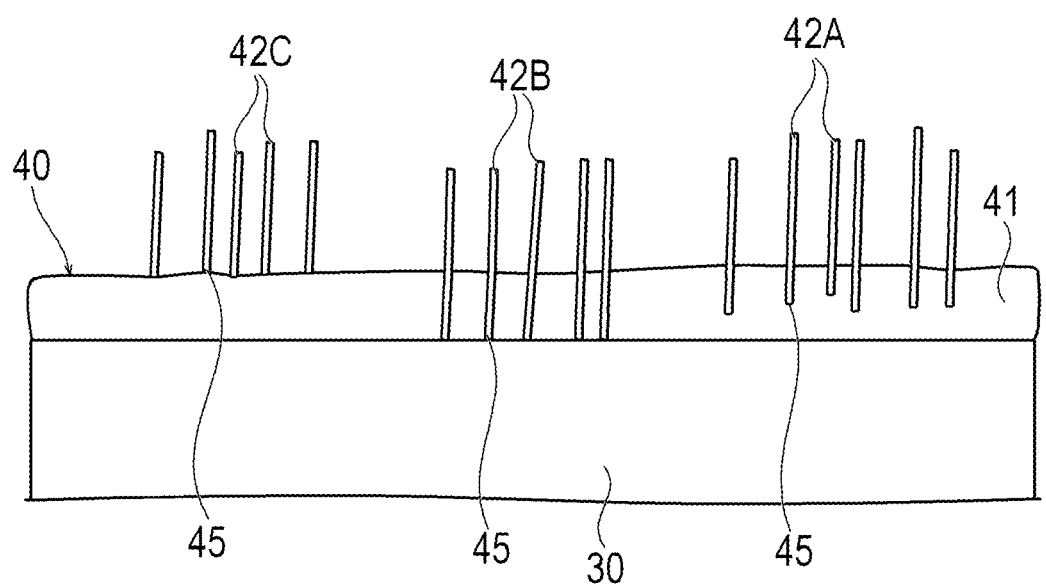
FIG. 14 is a cross-sectional view illustrating a modification example of the drug coating layer.

In addition, as in another modification example in FIG. 14, a drug coating layer 40 may have an additive layer 41, first elongated bodies 42A, second elongated bodies 42B, and third elongated bodies 42C. The first elongated body 42A extends from the inside of the additive layer 41 to the outside of the additive layer 41. The second elongated body 42B extends from an outer surface of the balloon 30 to the outside of the additive layer 41 by penetrating the additive layer 41. The third elongated body 42C extends from the outer surface of the additive layer 41 to an out-of-plane direction. The elongated body 42 may have only the first elongated body 42A. The elongated body 42 may have only the second elongated body 42B. The elongated body 42 may have the first elongated body 42A and the second elongated body 42B together.

The detailed description above describes embodiments of a method and apparatus for forming a drug coating layer provided on a surface of a balloon. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A method for forming a drug coating layer in which a plurality of elongated bodies which are crystals of a water-insoluble drug and each have a long axis are formed on a surface of a balloon, the method comprising:
supplying a coating solution which contains the water-insoluble drug, a water-soluble additive, an organic solvent, and water to the surface of the balloon and evaporating the organic solvent and the water to form an additive layer containing the water-soluble additive and a protruding crystal which is an elongated drug crystal having a tip end protruding from the additive layer;
forming a pleat portion protruding outward in a radial direction of the balloon after the protruding crystal is formed;
folding the pleat portion along a circumferential direction of the balloon;
cutting a surplus portion protruding from the additive layer of the protruding crystal from a part surrounded by the additive layer and forming the part surrounded by the additive layer as the elongated body in at least one of the forming of the pleat portion and the folding of the pleat portion by applying a force to the surplus portion; and
removing the cut surplus portion from the drug coating layer before the balloon is inserted into a living body.

2. The method for forming a drug coating layer according to claim 1, wherein the additive layer contains a water-soluble low molecular weight compound, wherein the water-soluble low molecular weight compound has a molecular weight of 50 to 2000.

3. The method for forming a drug coating layer according to claim 1, wherein in the removing of the cut surplus portion comprises:
removing the cut surplus portion from the drug coating layer by blowing gas to the surface of the balloon.

4. The method for forming a drug coating layer according to claim 1, wherein in the removing of the cut surplus portion comprises:
removing the cut surplus portion from the drug coating layer by applying vibration to the surface of the balloon.

5. The method for forming a drug coating layer according to claim 1, wherein the water-insoluble drug contains at least one water-insoluble drug selected from a group consisting of rapamycin, paclitaxel, docetaxel, and everolimus.

6. The method for forming a drug coating layer according to claim 1, wherein the balloon is part of a balloon catheter, the balloon catheter being a rapid exchange type balloon catheter or an over-the-wire type balloon catheter.

7. The method for forming a drug coating layer according to claim 1, wherein the elongated drug crystals comprises one or more of first elongated bodies, second elongated bodies, and third elongated bodies, the first elongated body extending from an inside of the additive layer to an outside of the additive layer, the second elongated body extending from the outer surface of the balloon to the outside of the additive layer by penetrating the additive layer, and the third elongated body extending from an outer surface of the additive layer to an out-of-plane direction.

8. The method for forming a drug coating layer according to claim 3, wherein the gas is helium gas, $CO_2$ gas, $O_2$ gas, $N_2$ gas, Ar gas, air, or a mixture of the helium gas, the $CO_2$ gas, the $O_2$ gas, the $N_2$ gas, the Ar gas, and/or the air.

9. The method for forming a drug coating layer according to claim 1, further comprising:
removing the cut surplus portion from the drug coating layer by the blowing of gas to the surface of the balloon while vibrating of the surface of the balloon.

10. The method for forming a drug coating layer according to claim 1, wherein the balloon is part of a balloon catheter, the balloon catheter being a rapid exchange type balloon catheter or an over-the-wire type balloon catheter.

11. A method for forming a drug coating layer on a balloon of a balloon catheter, the method comprising:
supplying a coating solution which contains a water-insoluble drug, a water-soluble additive, an organic solvent, and water to a surface of the balloon;
evaporating the organic solvent and the water from the coating solution to form an additive layer containing the water-soluble additive and protruding elongated drugs crystals having a tip end protruding from the additive layer;
forming a pleat portion protruding outward in a radial direction of the balloon after the protruding crystal is formed;
folding the pleat portion along a circumferential direction of the balloon;
cutting a surplus portion protruding from the additive layer of the protruding crystal from a part surrounded by the additive layer and forming the part surrounded by the additive layer as the elongated body in at least one of the forming of the pleat portion and the folding of the pleat portion by applying a force to the surplus portion; and
removing the cut surplus portion from the drug coating layer by one or more of blowing gas to the surface of the balloon and vibrating the surface of the balloon.

12. The method for forming a drug coating layer according to claim 11, wherein the additive layer contains a water-soluble low molecular weight compound, wherein the water-soluble low molecular weight compound has a molecular weight of 50 to 2000.

13. The method for forming a drug coating layer according to claim 11, wherein the water-insoluble drug contains at least one water-insoluble drug selected from a group consisting of rapamycin, paclitaxel, docetaxel, and everolimus.

14. The method for forming a drug coating layer according to claim 11, wherein the balloon is part of a balloon catheter, the balloon catheter being a rapid exchange type balloon catheter or an over-the-wire type balloon catheter.

15. The method for forming a drug coating layer according to claim 11, wherein the elongated drug crystals comprises one or more of first elongated bodies, second elongated bodies, and third elongated bodies, the first elongated body extending from an inside of the additive layer to an outside of the additive layer, the second elongated body extending from the outer surface of the balloon to the outside of the additive layer by penetrating the additive layer, and the third elongated body extending from an outer surface of the additive layer to an out-of-plane direction.

16. The method for forming a drug coating layer according to claim 11, wherein the gas is helium gas, $CO_2$ gas, $O_2$ gas, $N_2$ gas, Ar gas, air, or a mixture of the helium gas, the $CO_2$ gas, the $O_2$ gas, the $N_2$ gas, the Ar gas, and/or the air.

17. The method for forming a drug coating layer according to claim 11, further comprising:
- removing the cut surplus portion from the drug coating layer by the blowing of gas to the surface of the balloon while vibrating of the surface of the balloon.

* * * * *